United States Patent [19]
Rinehart et al.

[11] Patent Number: 6,153,731
[45] Date of Patent: Nov. 28, 2000

[54] DEHYDRODIDEMNIN B

[75] Inventors: Kenneth L. Rinehart, Urbana, Ill.;
Anna M. Lithgow-Bertelloni,
Salamanca, Spain

[73] Assignee: Pharma Mar, s.a., Madrid, Spain

[21] Appl. No.: 09/183,024

[22] Filed: Oct. 30, 1998

Related U.S. Application Data

[62] Division of application No. 08/280,110, Jul. 25, 1994, Pat. No. 5,834,586, which is a continuation of application No. 07/844,567, Apr. 24, 1992, abandoned.

[30] Foreign Application Priority Data

Jan. 10, 1990 [WO] WIPO ............... PCT/GB90/01495

[51] Int. Cl.⁷ .................................................... C07K 1/14
[52] U.S. Cl. ..................... 530/345; 530/344; 530/857
[58] Field of Search ........................... 530/345, 344, 530/317, 857

[56] References Cited

U.S. PATENT DOCUMENTS 4,493,796  1/1985  Rinehart, Jr. ............................ 530/317

OTHER PUBLICATIONS

Rinehart et al, J. Am. Chem. Soc., vol. 109, pp. 6846–6848 (1987).
K. L. Rinehart, Jr., *J. Am. Chem. Soc.* vol. 103, pp. 1857–1859, (1981).
Montgomery, D. W., Zukoski, C. F., *Trasnplantation*, vol. 40, pp. 49–56 (1985).
Montgomery et al., *Fed. Prac.*, vol. 44, p. 634 (1987).
Rinehart, Jr. et al., *Pure and Appl. Chem.*, vol. 54, pp. 2409–2424 (1982).
Rinehart, *ESCOM*, "Didemnin and Its Biological Properties", pp. 626–631, (1987).

*Primary Examiner*—Keith MacMillan
*Assistant Examiner*—T. D. Wessendorf

*Attorney, Agent, or Firm*—Ernest V. Linek; Banner & Witcoff, Ltd.

[57] ABSTRACT

Dehydrodidemnin B with useful biological activity has formula (1). It can be isolated from natural sources or synthesized, and it forms active derivatives.

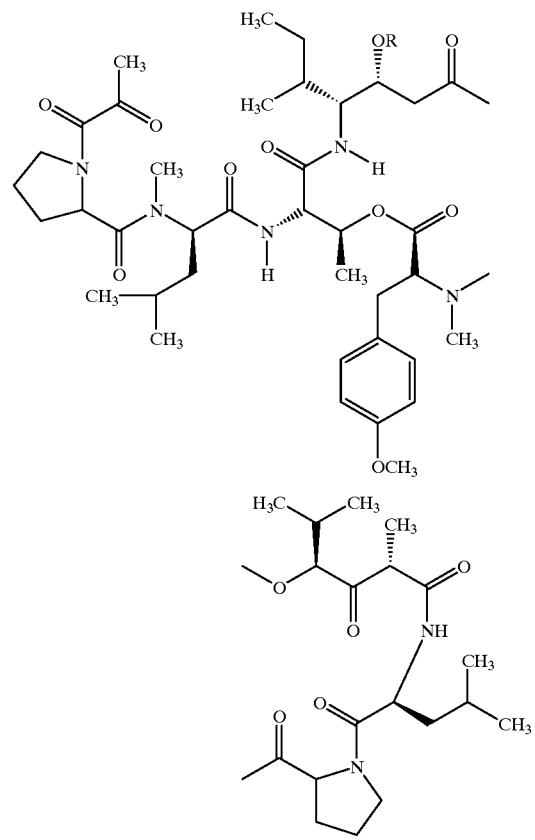

FORMULA I

2 Claims, 15 Drawing Sheets

DEHYDRODIDEMNIN B

CROSS-REFERENCE TO RELATED APPLICATIONS

The present application is a divisional application from application U.S. Ser. No. 08/280,110, filed Jul. 25, 1994, now U.S. Pat. No. 5,834,586, which was a continuation of application U.S. Ser. No. 07/844,567, filed Apr. 24, 1992, now abandoned.

FIELD OF THE INVENTION

This invention relates to dehydrodidemnin B and, in particular, to the isolation of dehydrodidemnin B, a cyclic depsipeptide, from a tunicate of the Ascidiacea class. This novel compound has been shown to have antiviral, antitumoral and cytotoxic activities.

BACKGROUND OF THE INVENTION

The didemnins form a class of cyclic depsipeptides which have been isolated from various species of the Tridemnum genus. They have been shown to have potent activity against viruses and tumor cells (Rinehart, Jr., et al., *J. Am. Chem. Soc.*, 103, 1857–59 (1981). Didemnin B, up to now the most active compound of this class, has been shown to have potent immunosuppressive activity (Montgomery et al., *Transplantation*, 40, 49–56 (1985) and a more potent inhibition of binding of prolactin to human lymphocytes than other didemnin compounds (Montgomery et al., *Fed. Prac.*, 44, 634 (1987).

SUMMARY OF THE INVENTION

This invention provides a novel and more active compound of this class, unexpectedly isolated from the Mediterranean tunicate *Alpidium albicans*, namely dehydrodidemnin B (or "DDB"), having the formula:

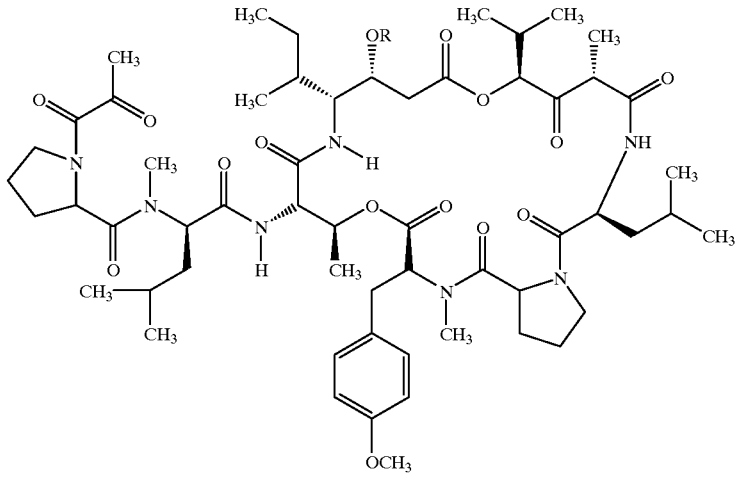

where R is hydrogen; and derivatives thereof with the same class of biological activity, i.e., where R is Acyl, Alkyl or Aryl.

DETAILED DESCRIPTION OF THE PREFERRED EMBODIMENTS

Figure 1A:
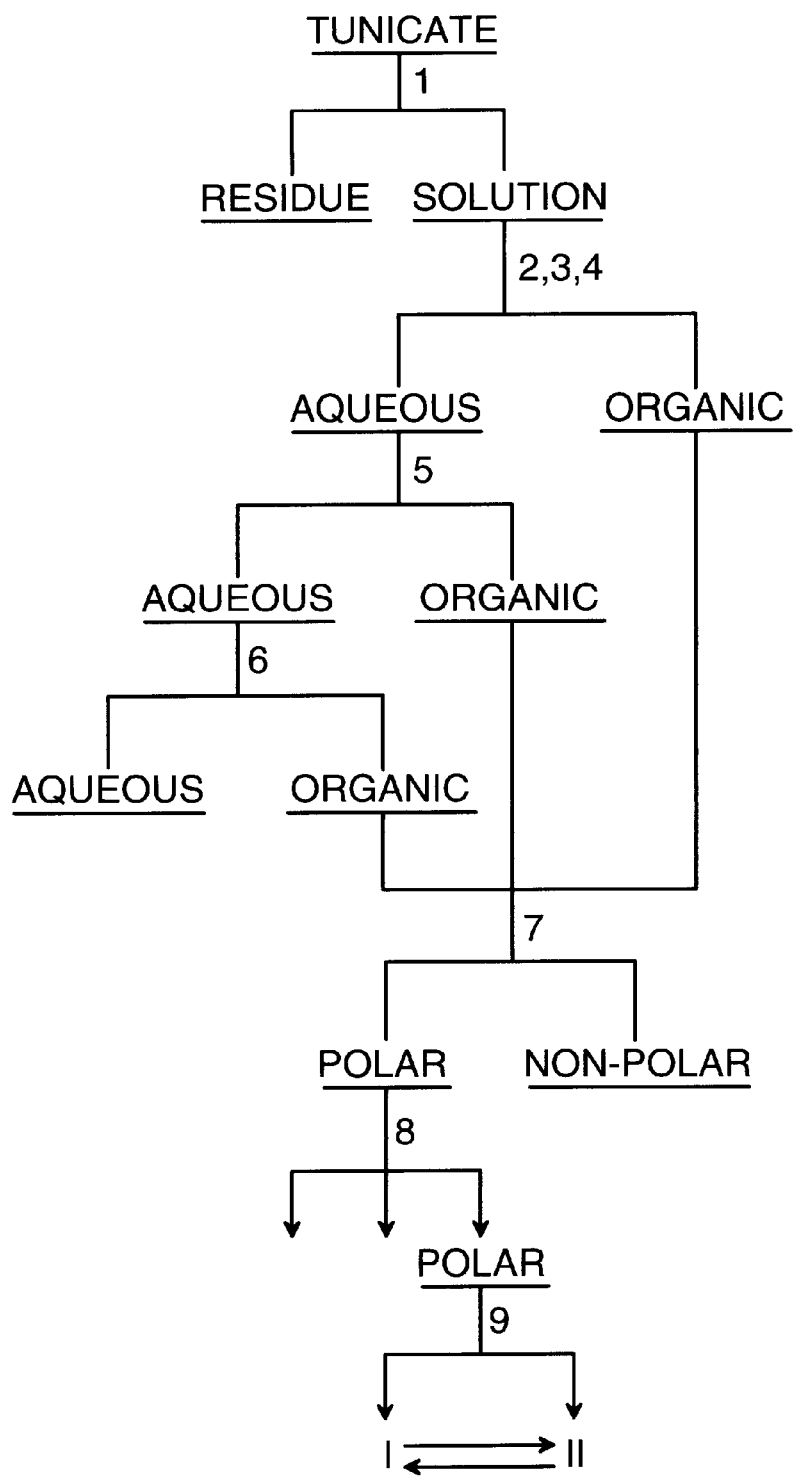
FIGS. 1A and 1B each illustrate a scheme by which DDB can be isolated from tunicates of the Ascidiacea class, subphylum Urochordata.

The compound of the present invention, DDB, is characterized by the following properties, considering also that, in solution, two conformers (at least) are possible:

TLC $R_f$=0.4; 0.35 (Silica gel, 2:3, $CH_2Cl_2$/EtOAc); 0.5; 0.44 (Silica gel; 9:1, $CHCl_3$/MeOH);

RP-HPLC $t_R$=10.7; 11.9 min (Spherisorb $C_{18}$ column, 250 mm×10 mm, 10µm particle size, 9.1, MeOH/$H_2$); 2 mL/min);

$[\alpha]_D^{25°}$=−86° (c 1, MeOH);

HR FABMS (M+M) $C_{57}H_{88}N_7O_{15}$ m/z calcd. 1110.6366; (M-side chain+H): $C_{42}H_{66}N_5O_{11}$ m/z calcd. 816.4781 (found 816.4755); (M-side chain): $C_{15}H_{23}N_2O_4$ m/z calcd. 295.1657 (found 295.1657);

IR ($CHCl_3$) vmax $cm^{-1}$ 3680, 3600, 2970, 2940, 2880, 1740, 1650, 1605, 1540, 1510;

$^1$H NMR ($CDCl_3$, δ, ppm): 7.82 (d, J=9 Hz, 1H); 7.79 (d, J=9 Hz, 1H); 7.62 (d, J=6 Hz, 1H); 7.21 (d, J=9 Hz, 1H); 7.19 (d, J-9 Hz, 1H); 7.08 (d, J=8.5 Hz, 2H); 6.85 (d, J=8.5 Hz, 2H); 3.77 (s, 3H); 3.13 (s, 3H); 3.08 (s, 3H); 2.54 (s, 3H); 2.50 (s, 3H); 2.1 (s, 3H); 2.02 (s, 3H); 0.82–0.88 (overlapped d and t, 30H); and $^{13}$C NMR ($CDCl_3$, δ, ppm): 204.93 (s); 204.77 (s); 201.23 (s); 197.55 (s); 173.05 (s); 173.05 (s); 172.36 (s); 171.84 (s); 171.21 (s); 171.16 (s); 170.59 (s); 169.58 (s); 169.51 (s); 169.35 (s); 168.36 (s); 168.28 (s); 161.31 (s); 161.06 (s); 158.64 (s); 158.62 (s), 130.31 (d); 114.12 (d); 114.01 (d); 81.47 (d), 81.43 (d); 70.68 (d); 70.33 (d); 67.97 (d); 67.76 (d); 66.38 (d); 66.22 (d); 60.39 (t); 50.88 (d); 57.80 (d); 66.38 (d); 66.22 (d);

60.39 (t); 50.88 (d); 57.80 (d); 57.45 (d); 57.26 (d); 57.18 (d); 57.12 (d); 55.61 (d); 55.57 (d); 55.26 (q); 54.65 (d); 49.55 (d); 49.49 (d); 48.85 (t); 48.41 (t); 46.98 (t); 41.29 (t); 41.24 (t); 38.78 (q); 38.74 (q); 38.68 (q); 36.42 (t); 36.22 (t); 34.06 (d); 33.99 (d); 33.96 (t); 31.57 (d); 31.38 (q); 31.34 (q); 31.30 (q); 30.69 (d); 29.68 (t); 29.64 (d); 27.28 (t); 27.94 (t); 27.30 (t); 27.17 (t); 27.08 (t); 25.91 (t); 25.87 (t); 25.73 (d); 25.68 (d); 25.63 (d); 25.52 (d); 25.48 (d); 24.80 (q); 24.70 (q); 24.44 (q); 24.31 (q); 22.21 (q); 22.12 (q); 21.92 (q); 21.79 (q); 21.76 (q); 19.46 (q); 17.76 (q); 17.72 (q); 17.18 (q); 16.87 (q); 16.08 (q); 15.62 (q); 15.48 (q); 15.05 (q); 12.55 (q); 12.50 (q).

The structure determination of DDB was accomplished by comparison of mass spectrometry low and high resolution FABMS (Rinehart, Jr. et al., *Pure and Appl. Chem.*, 54, 2409–2424 (1982)) and NMR data with other didemnin data, and confirmed by synthesis of DDB involving coupling of natural didemnin A with the appropriate side chain. The low resolution FAB mass spectra showed peaks at m/z 1110 (M+H), 816 (M+2H-side chain) and 295 (side chain). The lack of two mass units in the molecular ion and side chain peaks, in addition to the same m/z ratio for the ring, suggested that the difference between dehydrodidemnin B and didemnin B was represented by one more degree of unsaturation in the side chain. The molecular formula deduced from high resolution FABMS was $C_{57}H_{88}N_7O_{15}$ (M+H, $\Delta$2.8 mmu); and for the fragment ions corresponding to the ring and the side chain; $C_{42}H_{66}N_5O_{11}$ ($\Delta$0.4 mmu) and $C_{15}H_{23}N_2O_4$ ($\Delta$2.6 mmu), respectively. Tandem mass spectrometry on these peaks showed the typical cleavage pattern of didemnins.

From the NMR data, the presence of peptide linkages was indicated by peaks near $\delta$8 ppm and the methyl signals corresponding to the amino acid residues. Even though some of these peaks are doubled or tripled due to the presence of, at least two main conformers in solution at room temperature, these peaks are very similar to those of didemnins. The main difference observed between DDB and didemnin B is the methyl singlet peak at 2.04 ppm which could be assigned to a methyl ketone and the absence of the signal corresponding to the $\alpha$-proton of the hydroxyl group in the lactyl moiety at 4.3 ppm.

BIOLOGICAL ACTIVITIES

The compound of this invention has been shown to inhibit in vitro L1210 and P-388 mouse leukemia cells; L-929, mouse areolar and adipose tissue, B-16, mouse melanoma cells; A-549, human lung carcinoma cells; HeLa, human cervix epithelioid carcinoma cells and KB, human cervix epithelioid carcinoma cells and KB, human oral epidermoid carcinoma cells, and in vivo, P-338, mouse leukemia cells, Lewis lung carcinoma cells and B-16 melanoma cells. Thus, DDB is useful as an antitumor agent and therefore is useful inhibiting the growth of tumor cells in mammals exhibiting such tumor cells.

The following table summarizes the $IC_{50}$ values for each line cells in vitro:

TABLE 1

| Cell Line | $IC_{50}$ (ng/mL) |
|---|---|
| L-1210 | 0.3 |
| P-388 | 0.175 |
| L-929 | 1.9 |
| B-16 | 0.225 |
| A-549 | 0.5 |
| HeLa | 0.5 |
| KB | 5.6 |

The following table shows the % T/C in vivo after administration of DDB:

TABLE 2

| Dehydrodidemnin B in vivo Activity | | | |
|---|---|---|---|
| Compound | Control | DDB | DDB |
| Dose ($\mu$g/kg/injn) | — | 160 | 80 |
| Schedule and Route | QD 1–9, IF | QD 1–9, IP | QD 1–9, IP |
| P-388, Median Survival Time, Days | 10.0 | 21.0 | 19.5 |
| P-388% T/C$^a$ | 100 | 210 | 195 |
| Lewis Lung, Mean Tumor Volume mm$^3$ | 1512 1.00 | 0 0.00 | 189 0.13 |
| Lewis Lung % T/C$^b$ | | | |
| 3–16 Melanoma Median Survival Time Days | 17.0 | >27.0 | >27.0 |
| B-16 Melanoma % T/C$^a$ | 100 | >158 | >158 |

$^a$·Significant activity T/C $\geq$ 125.
$^b$·Significant activity T/C $\geq$ 0.40.

Dehydrodidemnin B, like didemnin B, (Montgomery et al., *Transplantation*, 40, 49–56 (1985)), is a powerful immunomodulator.

Dehydrodidemnin B has also shown activity against Herpes simplex virus, type 1, in CV-1 cells (monkey kidney cells); thus it is also useful as an antiviral agent. The $IC_{50}$ determined was 60 ng/mL (e.g., 10 fold greater than for L-1210 cells) and 1 $\mu$g/mL, respectively.

The compound of present invention is preferably presented for administration to humans and animals in unit dosage form in pharmaceutically appropriate carriers containing the active ingredient in the appropriate quantity.

Illustratively, dosage levels of the administered active ingredient can be intravenous 0.05 to about 50 mg/Kg, intraperitoneal, subcutaneous and intramuscular 1 to 100 mg/Kg; oral 1 to 150 mg/Kg of animal (body) weight.

The administration of DDB is useful to inhibit the growth of cancer cells in animals or humans bearing a neoplastic disease, for example, acute myelocytic leukemia, acute lymphocytic leukemia, malignant melanoma, adenocarcinoma of the lung, small cell carcinoma of the lung, and the like.

The compound can be isolated from tunicates of the genus Aplidium, and more especially from the species *Aplidium albicans*. The species is found in the Iberian Mediterranean Coast as well as in the Balearic Islands. The species has been also found in Great Britain, English Channel as well as in the Africa Coast and Portugal. It seems to prefer detritic, coralligenic and sciafilae algae communities. They also can be found in more photophilic habitats.

Colonies of the tunicate are generally flat and lobed (2.5 cm diameter). It is jelly like, totally encrusted with sand which confers a sandy color to the colony. Zooides are of a whitish color 10 mm long; the oral siphon has 6 lobes, and the cloacal languet is trifid, which is a species characteristic. Generally there are 10–11 rows of stigmas. The stomach has 6 marked folds. Gonads are of the family type with one or several ovocites below the digestive track and numerous testicular follicles forming one or double row in the post abdomen. Larvae are incubated in the number of 1 to 9 in the atrial cavity; they have 3 cupping-glasses and several vesicular formations in the anterior part.

Thus in a typical procedure in accordance with the present invention, isolation method generally comprises alcoholic extraction of the homogenized tunicate and selective purification of the desired DDB.

Figure 1B:
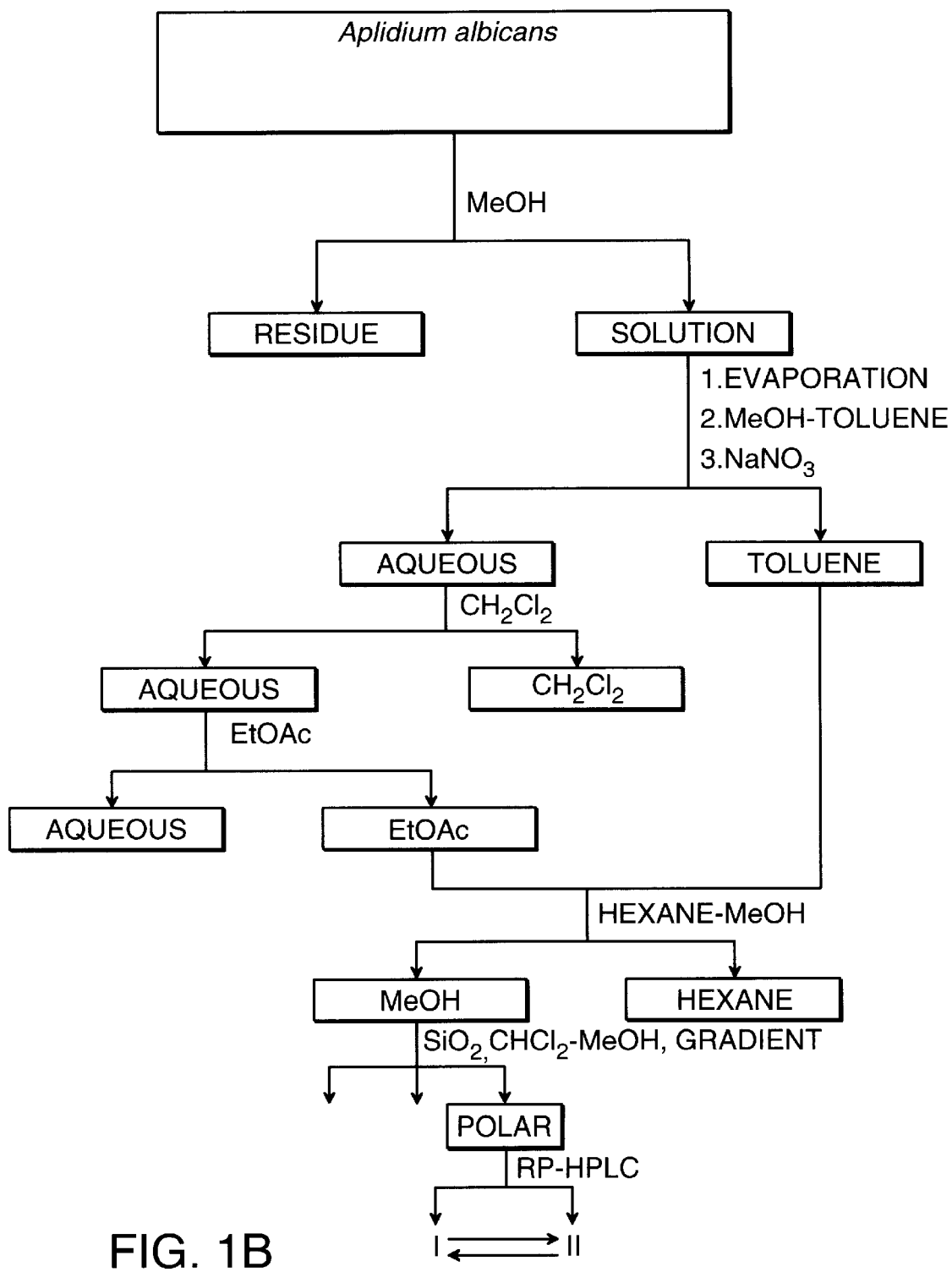
Figure 2:
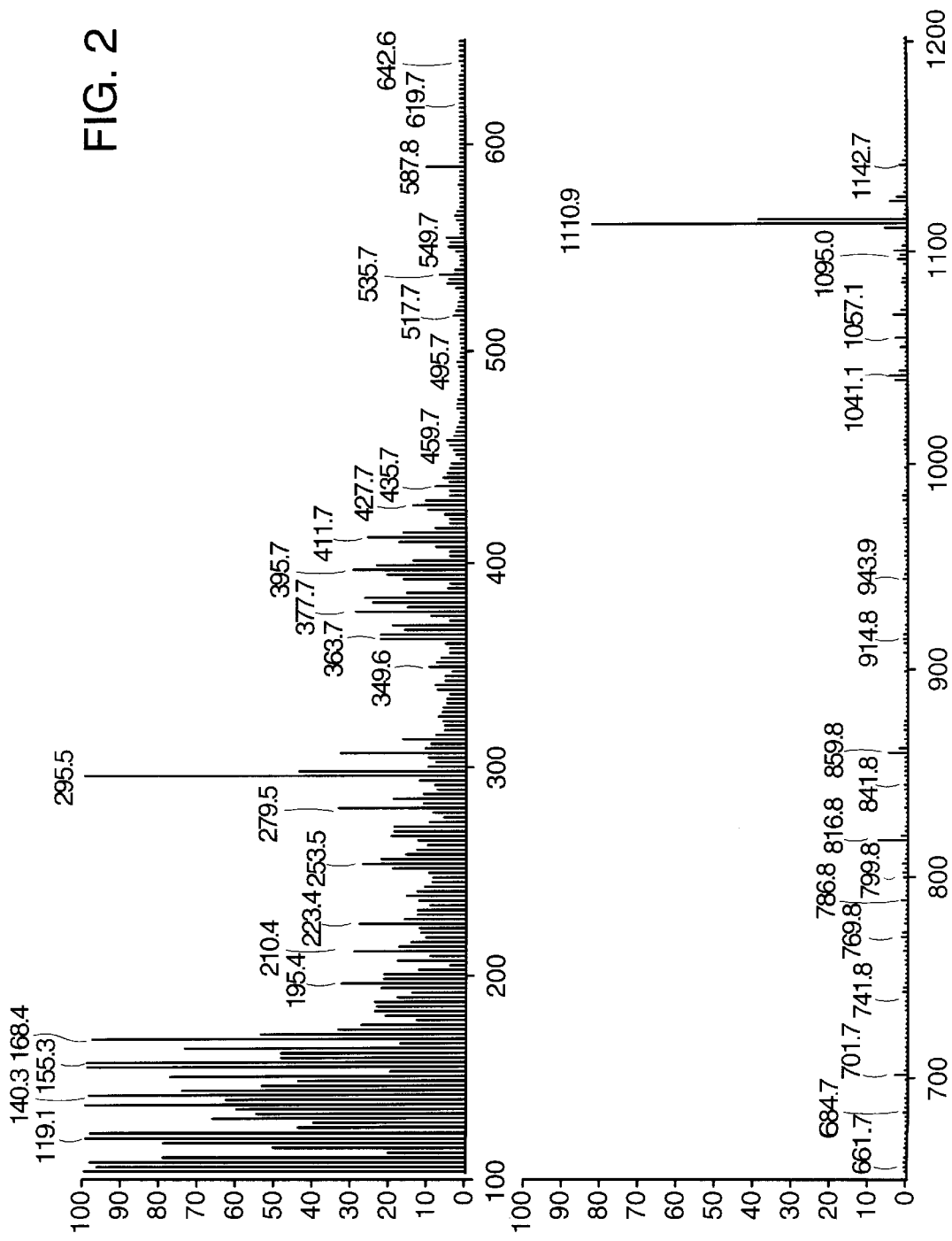
FIGS. 2–5 are mass spectra of compounds disclosed herein.
Figure 3:
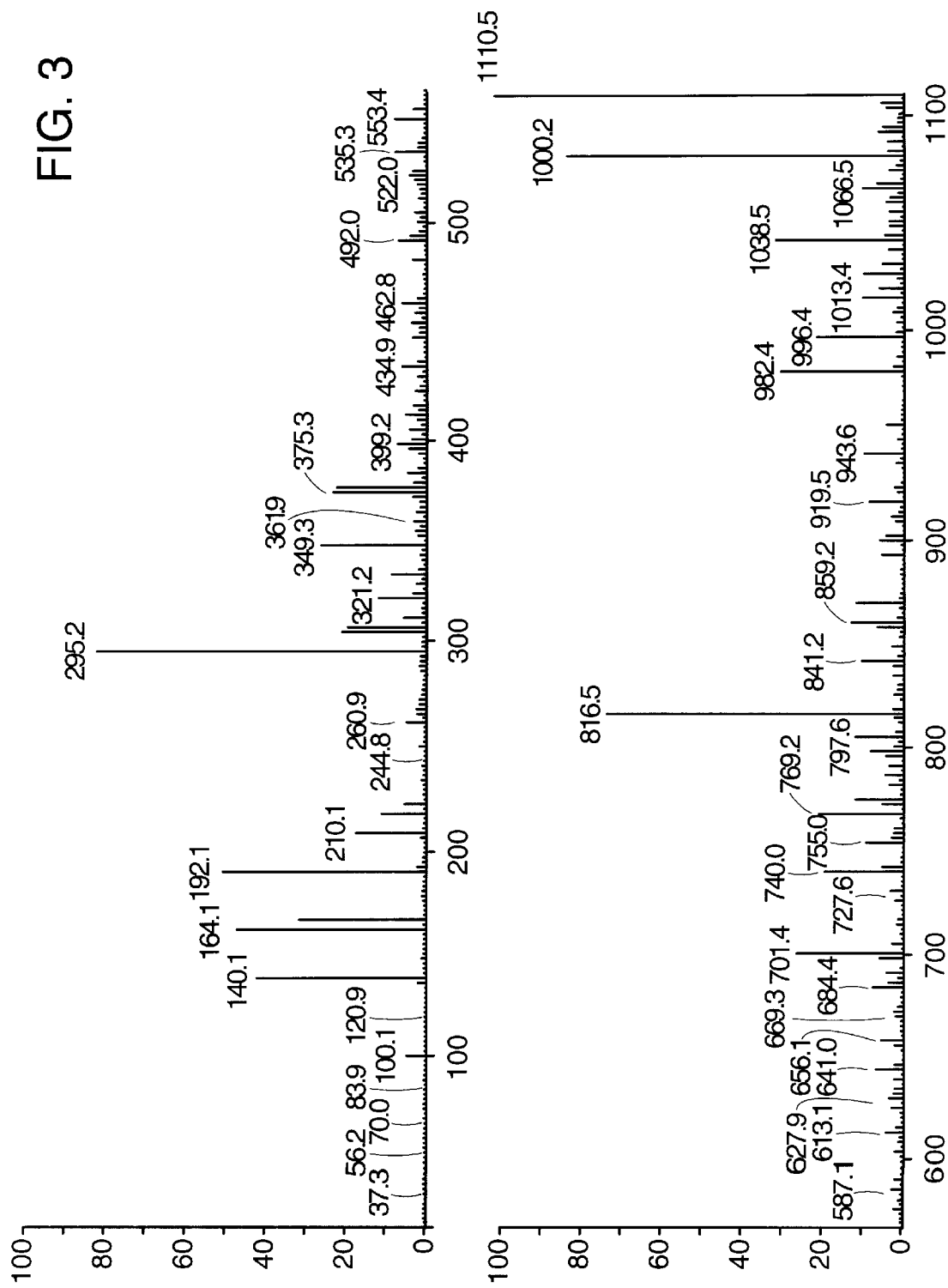
Figure 4:
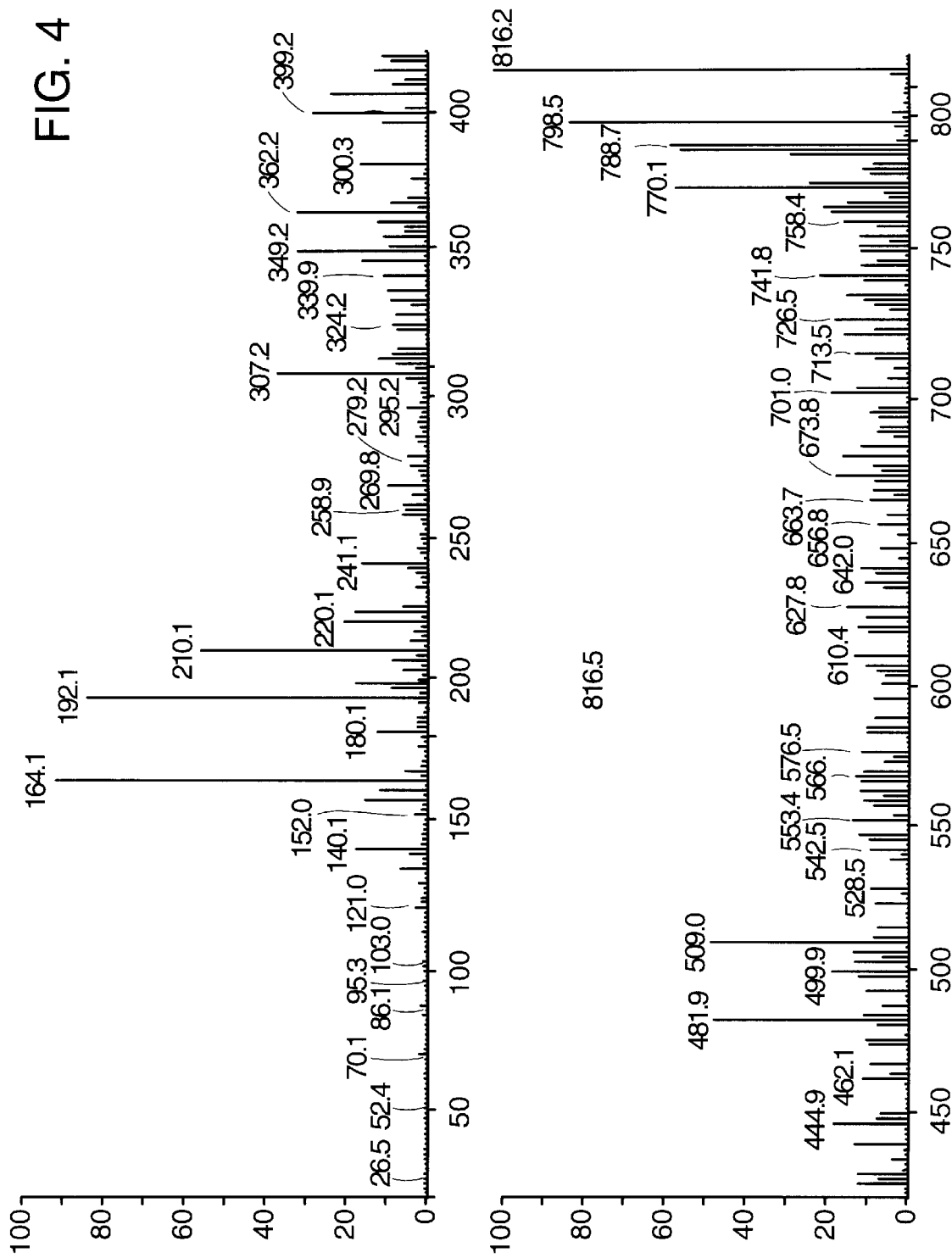
Figure 5:
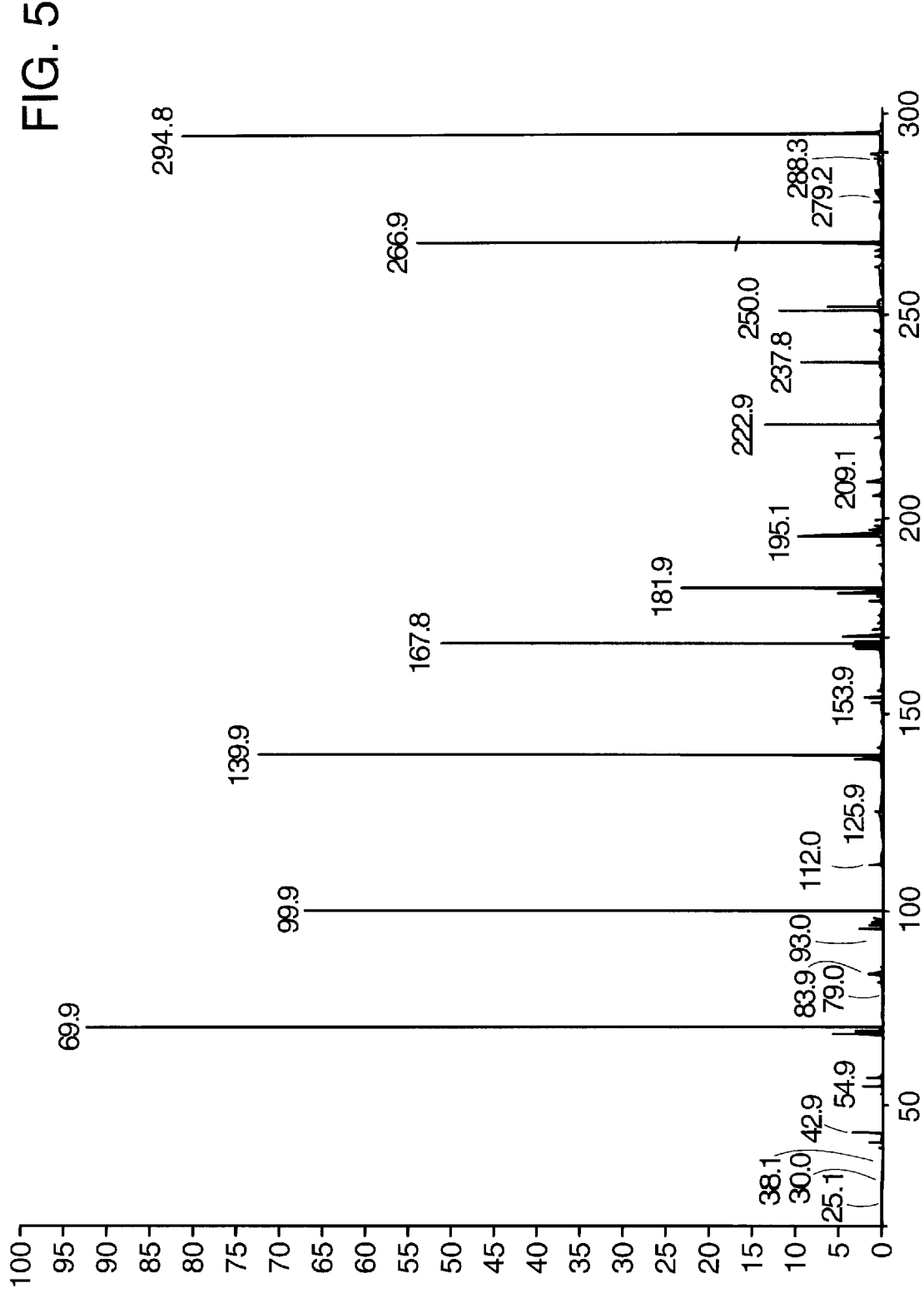
Figure 6:
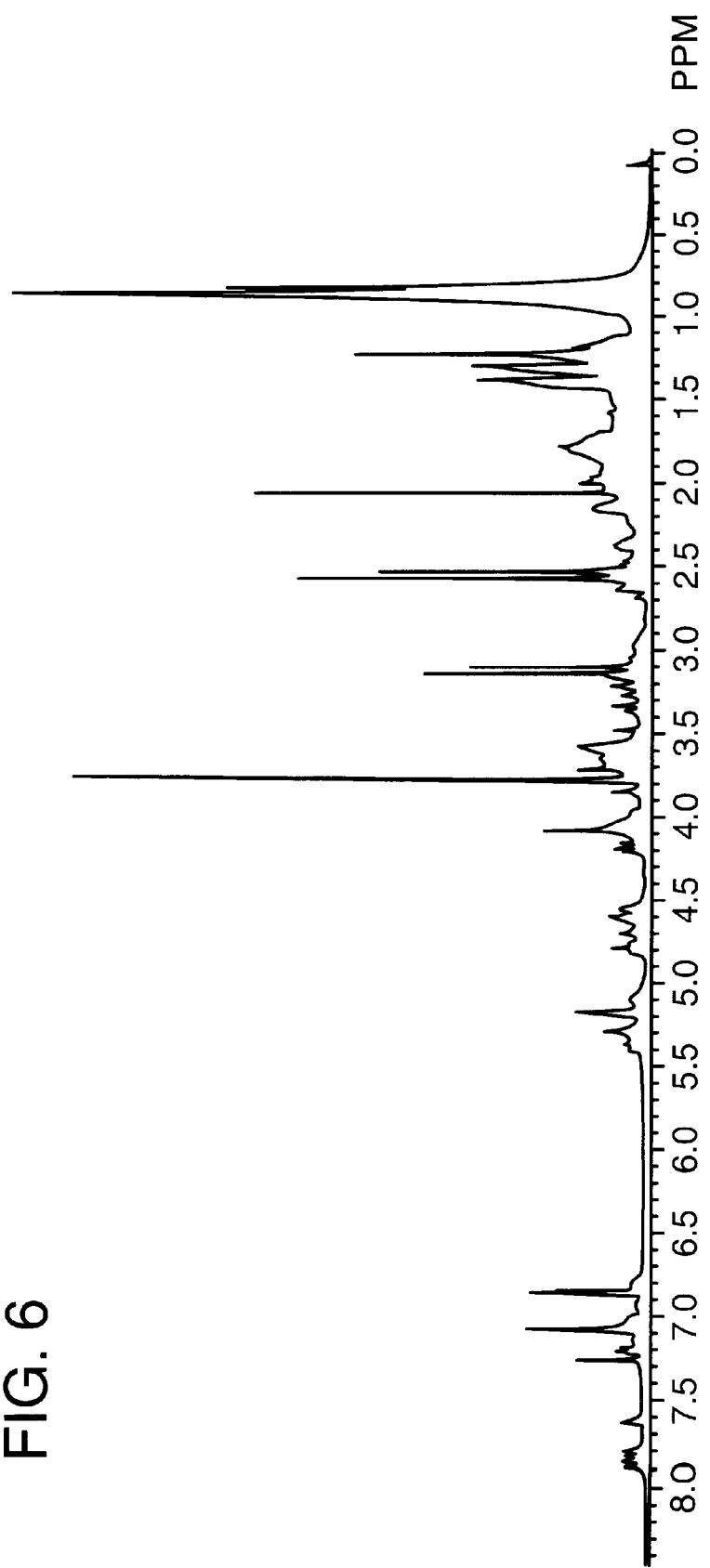
FIGS. 6 and 7–9 are $^1$H NMR spectra of compounds disclosed herein.
Figure 7:
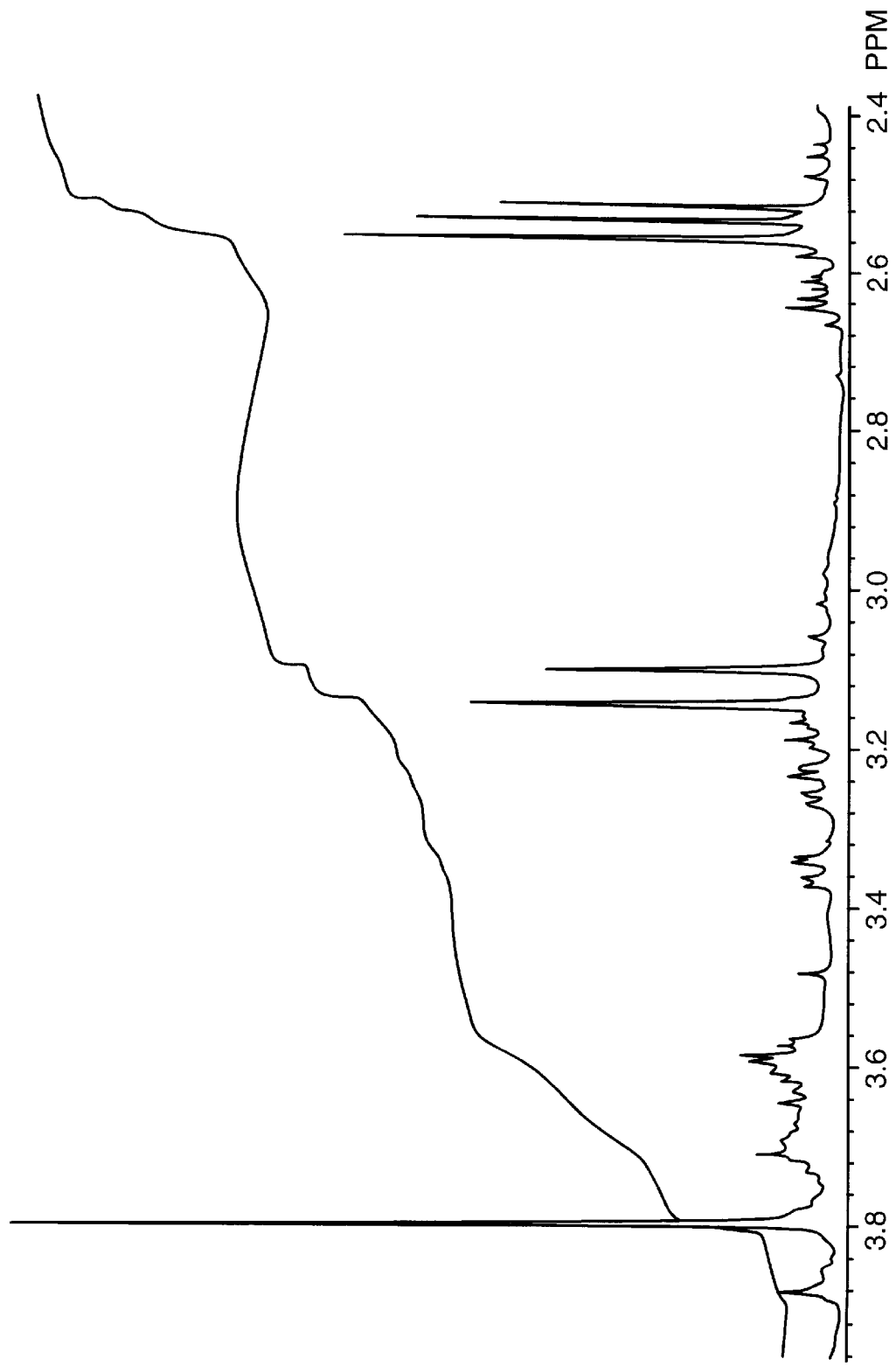
Figure 8:
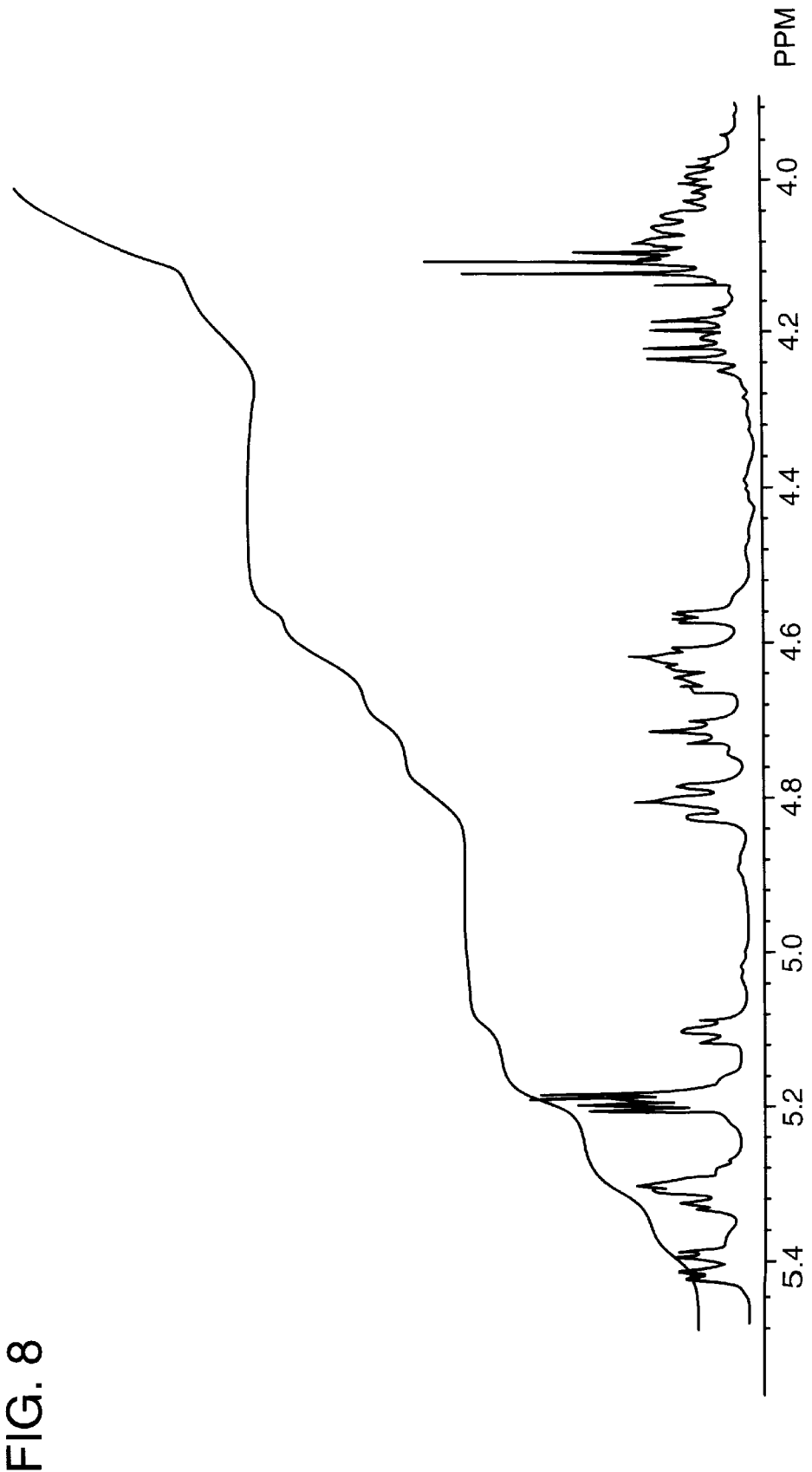
Figure 9:
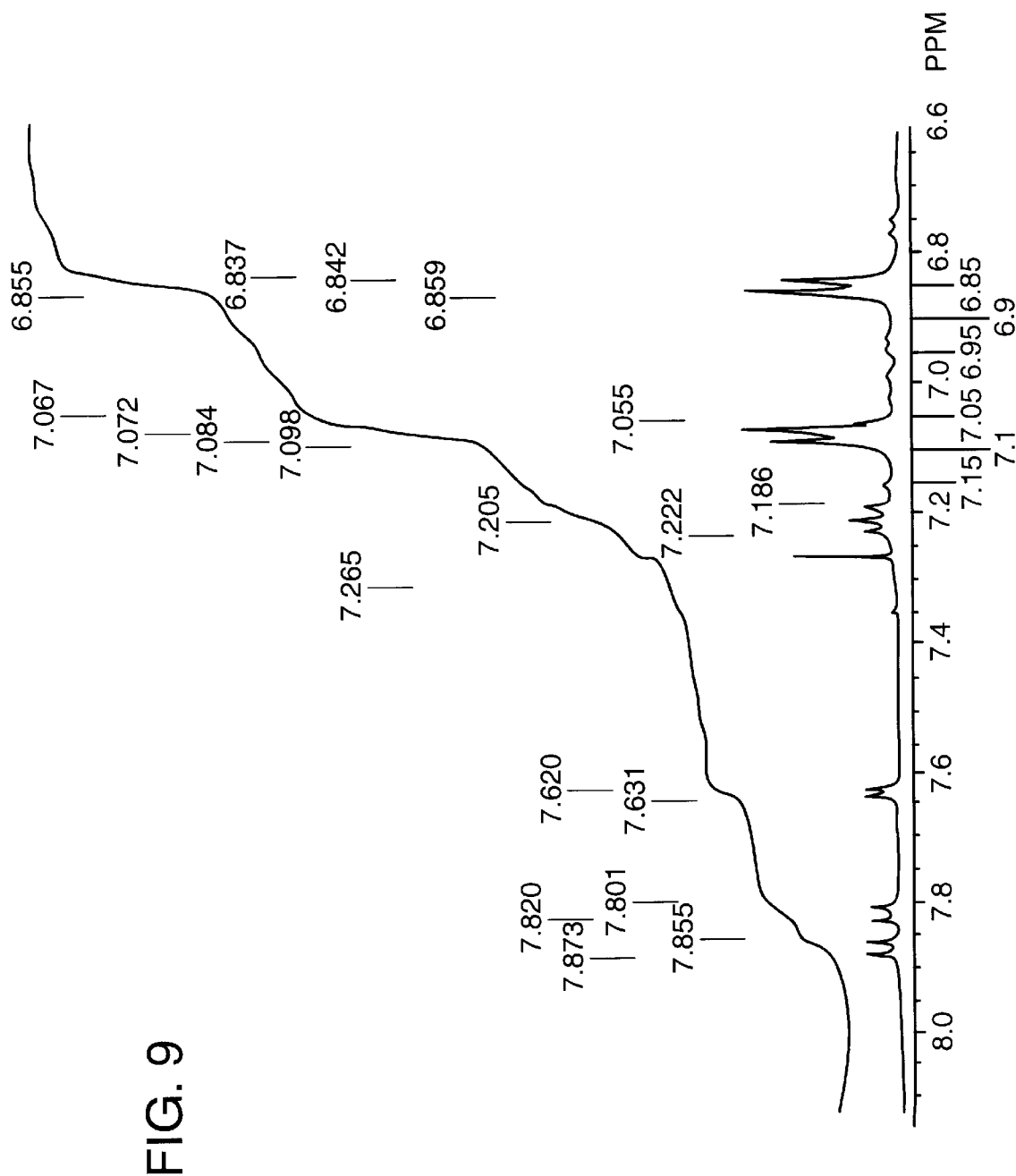
Figure 10:
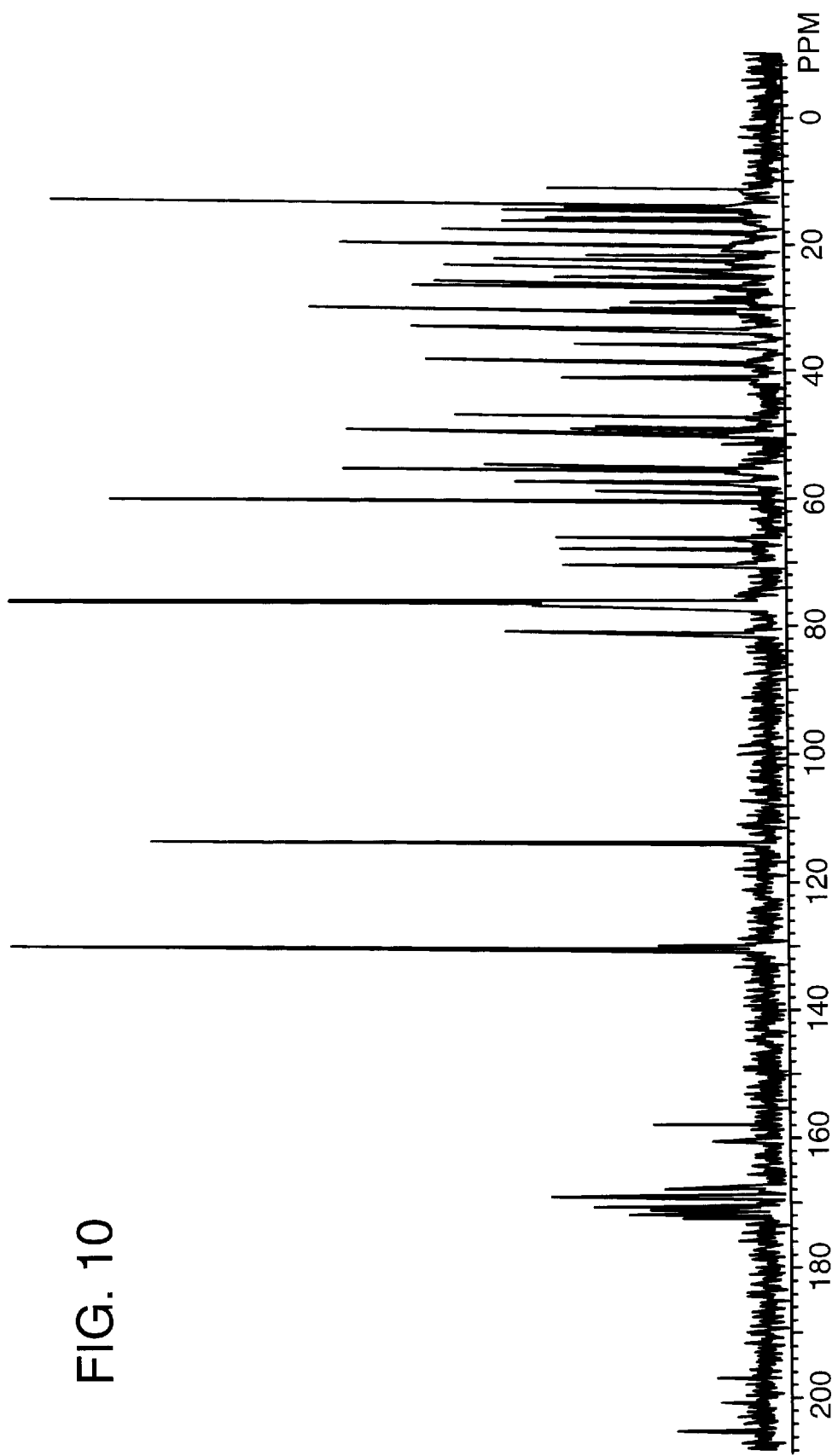
FIGS. 10 and 11–14 are $^{13}$C NMR spectrum of compounds disclosed herein.
Figure 11:
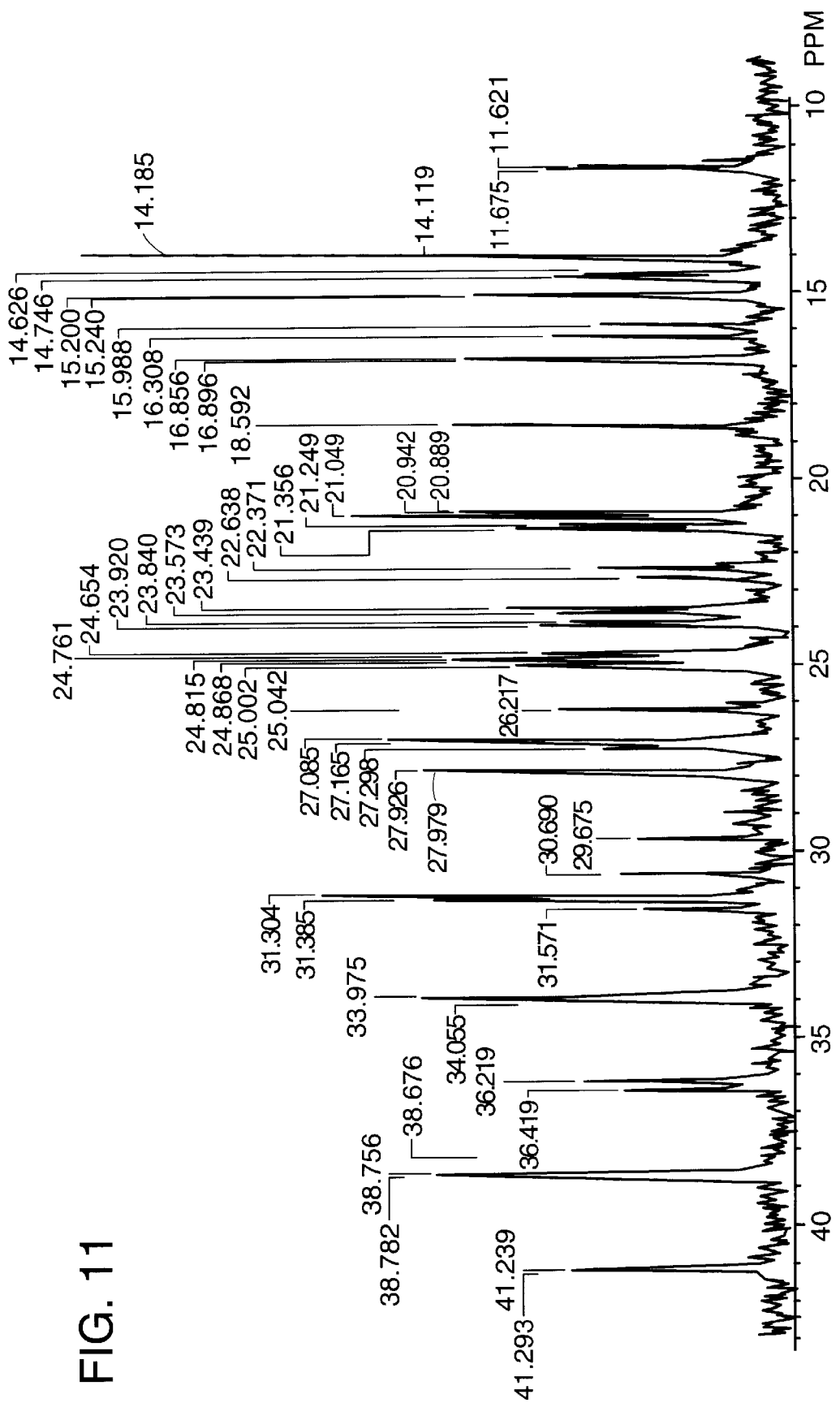
Figure 12:
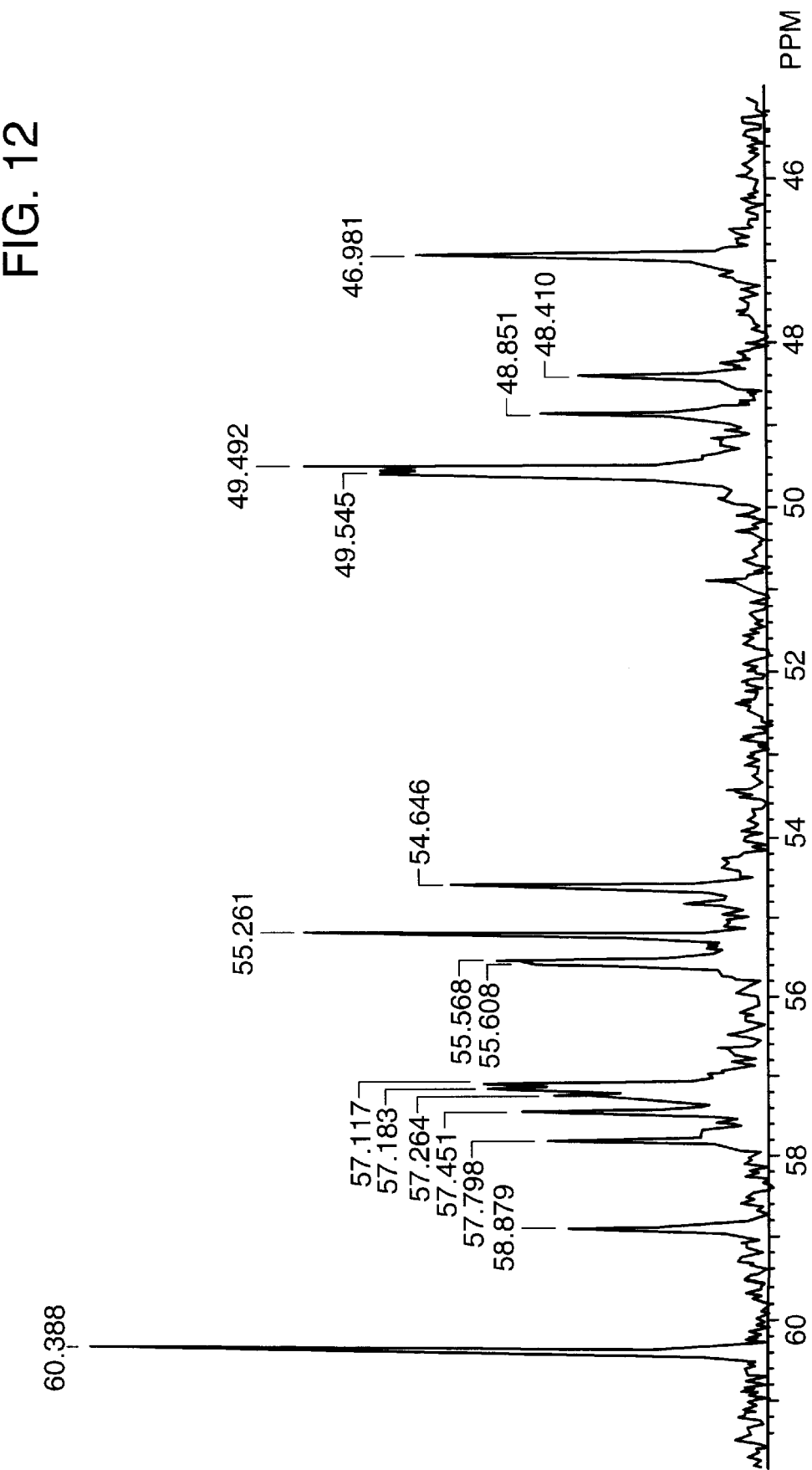
Figure 13:
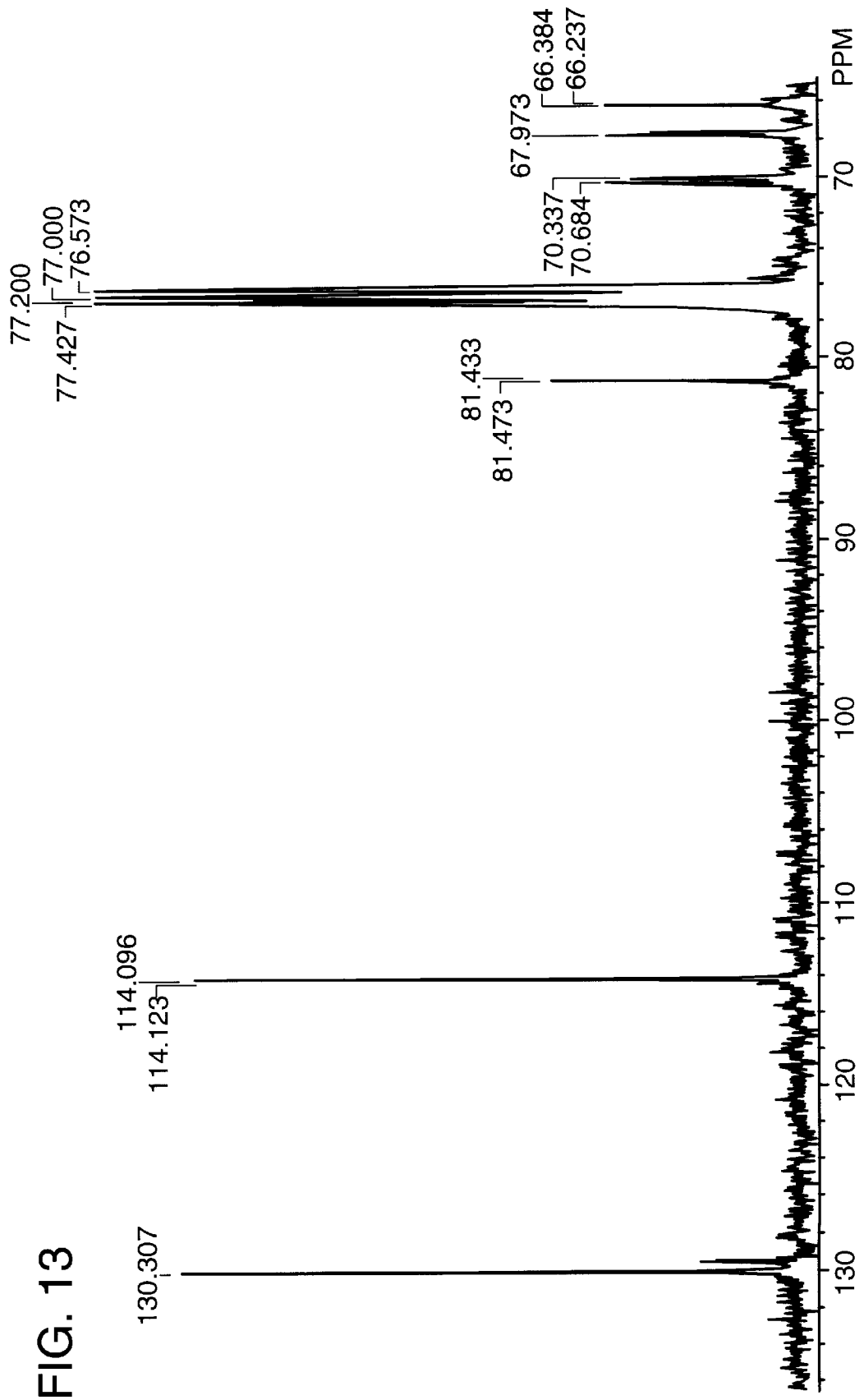
Figure 14:
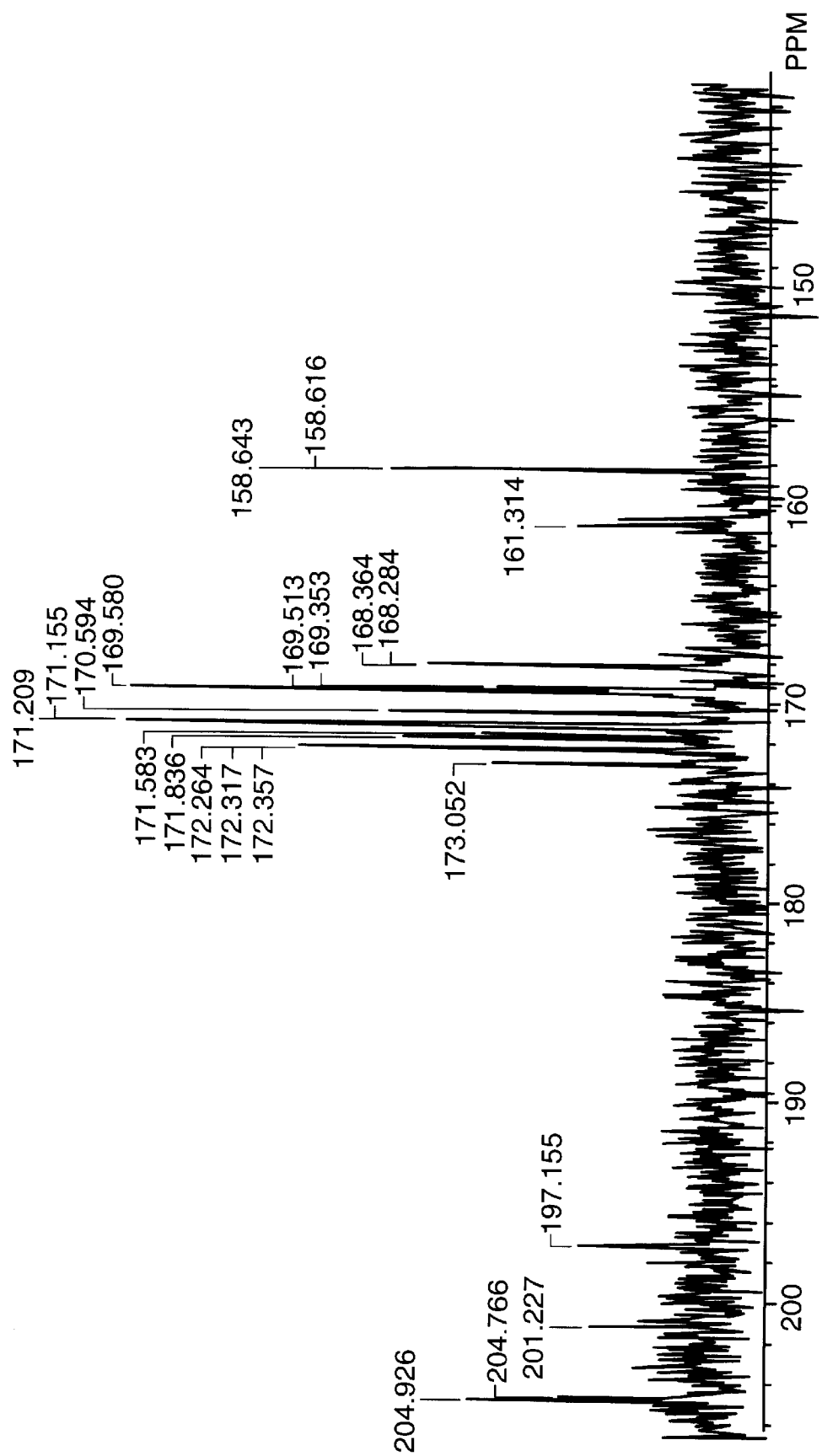

As shown in FIG. 1, the tunicate was extracted with MeOH, filtered and dissolved in MeOH: Toluene 3:1 and partitioned with 10% $NaNO_3$. The aqueous layer was successively extracted with $CH_2Cl_2$, EtOAc and n-BuOH. The organic fractions were combined after monitoring by normal-phase TLC developed $CHCl_3$:MeOH 9:1, affording a 2:1 (v/v) and the activity was concentrated in the methanolic layer. The polar fraction is passed through Silica gel Step-gradient Chromatography. The last fraction is further purified by reverse phase HPLC at a flow rate of 2 ml/min. Two mean peaks were collected and readily interconverted to a mixture of I and II, to establish an approximately 1:1 ratio.

The DDB can also be prepared by total synthesis, or semisynthesis from natural Didemnin A, following in both cases standard procedures of protection and activation in peptide chemistry.

Pyruvic acid +L-Pro→Side Chain
Side Chain +Didemnin A→Dihydrodidemnin B

Thus for example, Pro-OBzl, in DMF is mixed with pyruvic acid and HOBt, and DCC in $CH_2Cl_2$ added. The reaction product can be purified and shows the chemical and physical properties corresponding to Pyruvyl-Pro-OBzl.

To a solution of this last product in $CH_2Cl_2$, EDC and then Didemnin A was added. The evaporated residue is purified yielding DDB having chemical, physical, spectroscopical and biological characteristics in accord with natural Dehydrodidemnin B.

Apart from DDB itself, the present invention extends to derivatives of DDB, comprising acylated, alkylated or arylated derivatives of DDB, where R could be a group COR' or R', where R' represents the following substituents:

$CH_3$, $CHR_1R_2$, $CR_1R_2R_3$ or $C_6H_5$— where $R_1$ $R_2$, $R_3$, could be alkyl (either linear or branched), aryl or alkylaryl, the aryl groups, bearing or not the substituents described under R'. The residues $R_1$, $R_2$, $R_3$ could be either the same or different.

The derivatives can be more preferably alkyl, aryl or acyl-derivatives, where R' is an aliphatic or aromatic group, more preferably a 1–6 carbon atom residue.

In general, such derivatives from DDB of this kind, are expected to show similar biological activity to that of DDB itself, including specifically antitumoral, antiviral, cytotoxic and immunosuppressive activity.

The acyl derivatives can be obtained by treatment of the parent compound with the corresponding carboxylic anhydride in the presence of pyridine or other nitrogenated organic base; by reaction of DDB with the respective acylchloride; or by dehydration with DCC from DDB and the corresponding carboxylic acid.

In the case of the alkyl or aryl derivatives (R/R'), they can be obtained by reaction of DDB with the corresponding halide, in the presence of an alkaline-organic weak base or by dehydration between DDB and alkyl or aryl hydroxy derivative by an organic dehydrating agent.

Instrumentation, Material and Methods

NMR spectra were obtained with a General Electric QE-300 (300 MHz, $^1H$), a Nicolet NT-360 (360 MHz, $^1H$) or a General Electric GN 500 (500 MHz, $^1H$) at the University of Illinois or a Varian Unity 300 (300 MHz, $^1H$ and 75 MHz, $^{13}C$ at PharmaMar, S.A. (Madrid, Spain) Chemical shifts are reported in ppm referenced to the chloroform peak at a $\delta$7.26 ppm for $^1H$. FABMS were measured on a VG Analytical ZAB at the Mass Spectrometry laboratory of the University of Illinois. GC analyses were carried out using a Varian GC (Model 3700) equipped with an Alltech Associates, Inc., Chirasil-Val II capillary column (25 m×0.32 mm) with Helium gas carrier at a flow rate of 1.2 ml/min with programmed oven temperature (90° C., 4° C./min, 180° C.). Reversed-phrase HPLC was performed on a system equipped with an Altex pump (Model 110 A) and a Waters Associates differential refractometer (Model R-401) and an Alltech Spherisorb C18 column (25 cm×1 cm, particle size 10 $\mu$m) with MeOH: $H_2O$ 0:1 as the solvent system.

The following examples illustrate the invention.

EXAMPLE 1

Structure Determination

The structure of DDB has been determined by physical and spectroscopic methods.

1.1 Spectroscopic Data

TLC $R_f$=0.4; 0.35 (Silica gel, 2:3, $CH_2Cl_2$/EtOAc); 0,5; 0.44 (Silica gel; 9:1, $CHCl_3$/MeOH);

RP-HPLC $t_r$=10, 7; 11.9 min (Spherisorb $C_{18}$ column, 250 mm ×10 mm, 10 $\mu$m particle size, 9:1, MeOH/$H_2O$; 2 mL/min);

$[\alpha]_D^{25}$=86° (C 1, MeOH);

HR FABMS (M+H) $C_{57}H_{88}N_7O_{15}$ m/z calcd. 1110.6382 (found 1110.6366); (M-side chain+H): $C_{42}H_{66}N_5O_{11}$ m/z calcd. 816.4781 (found 816.4755): (M-side chain): $C_{15}H_{23}N_2O_4$ m/z calcd. 295.1657 (found 295.1657);

IR ($CHCl_3$) $v_{max}cm^{-1}$: 3680, 3600, 2970, 2940, 2880, 1740, 1650, 1605, 1540, 1510;

$^1H$ NMR ($CDCl_3$, $\delta$, ppm): 7.82 (d, J=9 Hz, 1H); 7.79 (d, J=9 Hz, 1H); 7.62 (d, J=6 Hz, 1H); 7.21 (d, J=9 Hz, 1H); 7.19 (d, J-9 Hz, 1H); 7.08 (d, J=8.5 H, 2H; 6.85 (d, J=8.5 Hz, 2H); 3.77 (s, 3H); 3.13 (s, 3H); 3.08 (s, 3H); 2.54 (s, 3H); 2.50 (s, 3H); 2.1 (s, 3H); 2.02 (s, 3H); 0.82–0.88 (overlapped d and t, 30H); $^{13}C$ NMR ($CDCl_3$, $\delta$, ppm): 204.93 (s); 204.77 (s); 201.23 (s); 197.55 (s); 173.05 (s); 173.05 (s); 172.36 (s); 171.16 (s); 170.59 (s); 169.58 (s); 169.35 (s); 168.36 (s); 168.28 (s); 161.31 (s); 161.06 (s); 158.64 (s); 158.62 (s), 130.31 (d); 114.12 (d); 114.10 (d); 81.47 (d), 81.43 (d); 70.68 (d); 70.33 (d); 67.97 (d); 67.76 (d); 66.38 (d); 66.22 (d); 60.39 (t); 50.88 (d); 57.80 (d); 66.38 (d); 66.22 (d); 60.39 (t); 50.88 (d); 57.80 (d); 57.45 (d);

57.26 (d); 57.18 (d); 57.12 (d); 55.61 (d); 55.57 (d); 55.26 (q); 54.65 (d); 49.55 (d); 49.49 (d); 48.85 (t); 48.41 (t); 46.98 (t); 41.29 (t); 41.24 (t); 38.78 (q); 38.74 (q); 38.68 (q); 36.42 (t); 36.22 (t); 34.06 (d); 33.99 (d); 31.57 (d); 31.38 (q); 31.34 (q); 31.30 (q); 30.69 (d); 29.68 (t); 29.64 (d); 27.28 (t); 27.94 (t); 27.30 (t); 27.17 (t); 27.08 (t); 25.91 (t); 25.87 (t); 25.87 (t); 25.73 (d); 25.68 (d); 25.63 (d); 25.52 (d); 25.48 (d); 24.80 (q); 24.70 (q); 24.44 (q); 24.31 (q); 24.44 (q); 22.21 (q); 22.12 (q); 21.92 (q); 21.79 (q); 21.76 (q); 19.46 (q); 17.76 (q); 17.72 (q); 17.18 (q); 16.87 (q); 16.08 (q); 15.62 (q); 15.48 (q); 15.05 (q); 12.55 (q); 12.50 (q).

1.2 Acetylation of DDB

The structure of dehydrodidemnin B can be confirmed also by comparison of the acetylation product with the acetyl derivative of didemnin B.

Acetylation of DDB with acetic anhydride and pyridine gave a monoacetyl derivative.

Low resolution mass spectrum showed peaks at ml z 1153.5 (M+H), 859.0 (M+2H-side chain) and 295.4 (side chain), indicating the loss of one of the two possible sites of acetylation with respect to didemnin B, and that the missing site is the hydroxyl group of the lactyl moiety in the side chain.

1.3 N-Trifluoroacetyl Methyl Esters of Amino Acid Residues

The structure of DDB can also be determined by identification of the individual subunits by total hydrolysis and conversion of the amino acids to their N-trifluoroacetyl methyl esters and analysis by GC.

The amino acids were identified by their retention times and comparison of authentic samples obtained from the conversion of didemnin B to the N-trifluoroacetyl methyl esters of the amino acids.

$t_R$ (min): L-Threonine (1.23); D-N-Me-Leucine (1.70); L-Leucine (2.05); L-Proline (2.38); (3S,4R,5S)-Isostatine (3.15, 4.13, 4.77); L-N,O-Me$_2$-Tyrosine (6.75).

A mixture of DDB and glass-distilled HCl was heated during 18 hours at 110° C. in a sealed Teflon-lined screw-capped vial. The solvent was removed under a stream of N$_2$ gas.

The hydrolysate was treated with MeOH/Acetyl chloride during 1 hour at 110° C. The solution was cooled to room temperature, the solvent was removed under a stream of N$_2$ gas. The solid was treated with a mixture of TFAA/TFA during 15 min at 100C. The solution, was cooled and the solvent evaporated. The residue was dissolved in 2-propanol for GC analysis.

EXAMPLE 2

Biological Activity Assays 2.1 Assay Against L-1210 Cells (Ascetic fluid from DBA/2mouse)

L-1210 cells were seeded into 16 mm wells at 1×10$^4$ cells per well in 1 mL aliquots of MEN 10C containing the indicated concentrations of drug. All determinations were carried out in triplicate. Cells were counted after three drugs was counted daily to ensure that the cells remained in exponential growth over the period of observation.

| Growth Inhibition of L-1210 cells by DDB | | |
|---|---|---|
| ng/mL DDB | net increase in cell number | % Inhibition |
| 0 | 2.9 × 10$^5$ | 0 |
| 0.05 | 2.7 × 10$^5$ | 7 |
| 0.1 | 2.7 × 10$^5$ | 7 |
| 0.2 | 2.1 × 10$^5$ | 28 |
| 0.5 | 1.0 × 10$^5$ | 66 |
| 1 | 2.5 × 10$^4$ | 91 |
| 2 | 6.3 × 10$^3$ | 98 |

2.2 Assay Against P-388 Cells (lymphoid neoplasm from DBA/2mouse)

P-388 cells were seeded into 16 mm wells at 1×10$^4$ cells per well in 1 mL aliquots of MEM 10C containing the indicated concentrations of drug. All determinations were carried out in triplicate. Cells were counted after three days of incubation. A separate set of cultures without drug was counted daily to ensure that the cells remained in exponential growth over the period of observation.

| Growth Inhibition of P-388 cells by DDB | | |
|---|---|---|
| ng/mL DDB | net increase in cell number | % Inhibition |
| 0 | 5.63 × 10$^5$ | 0 |
| 0.12 | 3.97 × 10$^5$ | 29 |
| 0.25 | 1.27 × 10$^5$ | 77 |
| 0.5 | 4.47 × 10$^5$ | 92 |

2.3 Assay Against L-929 Cells (mouse areolar and adipose tissue)

L-929 cells were seeded into 16 mm wells at 1×10$^4$ cells per well in 1 mL aliquots of MEM 10C. The following day, medium was replaced with 0.5 mL aliquots of MEM 10C. The following day, the medium was replaced with 0.5 mL aliquots of MEM 10C containing the indicated concentrations of drug. All determinations were carried out in triplicate. A separate set of cultures without drug was counted daily to ensure that the cells remained in exponential growth over the period of observation. Cells were trypsinized and counted 4 days after seeding.

| Growth Inhibition of L-929 cells by DDB | | |
|---|---|---|
| ng/mL DDB | net increase in cell number | % Inhibition |
| 0 | 3.17 × 10$^5$ | 0 |
| 1 | 2.31 × 10$^5$ | 27 |
| 2.5 | 1.13 × 10$^5$ | 64 |
| 5 | 5 × 10$^5$ | 84 |

2.4 Assay Against B-16 Cells (mouse melanoma)

B-16 cells were seeded into 16 mm wells at 1×10$^4$ cells per well in 1 mL aliquots of MEM 10C determinations were carried out in triplicate. A separate set of cultures without drug was counted daily to ensure that the cells remained in exponential growth over the period for observation. Cells were trypsinized and counted 4 days after seeding.

| Growth Inhibition of B-16 cells by DDB | | |
|---|---|---|
| ng/mL DDB | net increase in cell number | % Inhibition |
| 0 | $1.71 \times 10^5$ | 0 |
| 0.16 | $1.71 \times 10^5$ | 0 |
| 0.12 | $1.27 \times 10^5$ | 25 |
| 0.25 | $8.25 \times 10^4$ | 54 |
| 0.5 | $4.50 \times 10^4$ | 74 |
| 1.0 | $2.88 \times 10^4$ | 83 |

2.5 Assay Against A-549 Cells (human lung carcinoma)

A-549 cells were seeded into 16 mm wells at $1\times10^4$ cells per well in 1 mL aliquots of MEM 10C. The following day, the medium was replaced with 0.5 mL aliquots of MEM 10C containing the indicated concentrations of drug. All determinations were carried out in triplicate. A separate set of cultures without drug was counted daily to ensure that the cells remained in exponential growth over the period of observation. Cells were trypsinated and counted 4 days after seeding.

| Growth Inhibition of A-549 cells by DDB | | |
|---|---|---|
| ng/mL DDB | net increase in cell number | % Inhibition |
| 0 | $8.16 \times 10^4$ | 0 |
| 0.25 | $4.80 \times 10^4$ | 41 |
| 0.50 | $4.00 \times 10^4$ | 50 |
| 1.0 | $2.50 \times 10^4$ | 68 |
| 2.5 | $1.30 \times 10^4$ | 84 |

2.6 Assay Against HeLa Cells (human cervix epithelioid carcinoma)

HeLa cells were seeded into 16 mm wells at $1\times10^4$ cells per well in 1 mL aliquots of MEM 10C. The following day, the medium was replaced with 0.5 mL aliquots of MEM 10C containing the indicated concentrations of drug. All determinations were carried out in triplicate. A separate set of cultures without drug was counted daily to ensure that the cells remained in exponential growth over the period of observation. Cells were trypsinized and counted 4 days after seeding.

| Growth Inhibition of KB cells by DDB | | |
|---|---|---|
| ng/mL DDB | net increase in cell number | % Inhibition |
| 0 | $4.50 \times 10^4$ | 0 |
| 2.5 | $4.57 \times 10^4$ | 0 |
| 5 | $2.40 \times 10^4$ | 46 |
| 10 | $1.02 \times 10^4$ | 77 |

2.8 Assay Against HSV-1 (Herpes simplex virus type-1)

16 mm diameter wells were seeded each with $2\times10^5$ CV-1 cells in 1 mL aliquots of MEM 10C. Four days after, cells were infected with HSV-1 at 10C PFU per well. After adsorption for 1.5 hours, the inoculum was replaced in pairs of wells with 0.5 mL aliquots of MEM 5C containing the indicated concentrations of drug. Cells from two wells without drug were scraped into the medium and frozen 4 hours after infection to provide a baseline for calculating new virus production. The average of these samples was $2.5\times10^5 + 1.2\times10^6$ PFU per mL. The remaining samples were collected 24 hours after infection.

| Inhibition of HSV-1 replication by DDB | | |
|---|---|---|
| ng/mL DDB | net virus produced (PFU/mL) | % Inhibition |
| 0 | $4.5 \times 10^8$ | 0 |
| 0.03 | $3.8 \times 10^8$ | 16 |
| 0.1 | $1.5 \times 10^8$ | 67 |
| 0.3 | $1.9 \times 10^8$ | 96 |
| 1 | 0 | 100 |

2.9 Immunosuppressive Activity

Dehydrodidemnin B is active as an immunosuppressive agent. In the mixed lymphocyte reaction it suppresses the immune reaction of murine cells. It also inhibits the growth of murine T-cells and B-cells.

EXAMPLE 3

Extraction and Isolation

A white solitary tunicate was collected near Ibiza in the Balearic Islands (Spain) and was identified by Dr. Xavier Turon of the Universitat de Barcelona, Barcelona (Spain) as *Aplidium albicans*. A sample is preserved at Centre d'Etudes Avancats, Blanes (Germona, Spain). Preliminary tests on shipboard indicated antiviral activity against VSV-1 (Vesicular stomatitis virus). Further studies in the laboratory confirmed the antiviral activity against Herpes simplex virus, type 1 (HSV-1) in monkey kidney cells (CV-1) and also showed cytotoxicity against mouse lymphoid leukemia in vitro (L1210 line cells).

The frozen tunicate was extracted with methanol. Solvent partitioning of the residue afforded three active fractions which were combined according to their similarity in TLC (Thin Layer Chromatography). The crude active fraction was portioned and the activity concentrated in the methanolic layer. The methanol layer was chromatographed by silica gel gravity column (chloroform and chloroform-methanol mixtures), affording one active fraction which was further purified by Reversed-Phase High-Performance Liquid Chromatography ($RPC_{18}HPLC$), affording two peaks (I and II). Analysis by TLC revealed two identical spots in each HPLC fraction. Re-injection of each individual fraction led to two peaks with the same retention times as I and II. Co-injection of I and II confirmed the presence of two identical peaks (possible conformers) in each fraction suggesting a rapid interconversion of I to II and vice versa.

EXAMPLE 4

Semisynthesis of DDB from Didemnin A

Dehydrodidemnin B can also be obtained and its structure confirmed by comparison with a semisynthetic sample prepared by coupling of the appropriate side chain to natural didemnin A. The data obtained for the semisynthetic sample totally agreed with data for natural DDB.

4.1 Synthesis of Pyruvyl-Pro-)Bzl

The hydrochloride salt of Pro-OBzl (10.2 g, 42 mmol) was dissolved in dry DMF (30 ml), neutralized with NMM (N-methylmorpholine, 4.7 mL, 42 mmol) at 0° C., and the solution was mixed with pyruvic acid (8.8 g, 100 mmol) and HOBt (1-hydroxybenzotriazole, 16.8 g, 110 mmol) in $CH_2Cl_2$-DMF (90 mL, 8:1). DCC (dicyclohexylcarbodiimide, 22.6 g, 110 mmol) in $CH_2Cl_2$ (35 mL) was added to the above mixture at 0° C. with stirring. The reaction mixture was stirred for 2 hours at 0° C. and left overnight at room temperature. DCCI was filtered off and washed with $CH_2Cl_2$ (20 mL). The filtrate was evaporated to dryness, the residue taken up in EtOAc and washed successively with 5% citric acid, water, 5% $NaHCO_3$ and finally with water to neutral pH. The organic layer was dried ($Na_2SO$) and concentrated. The residue was chromatographed on $SiO_2$ with hexane-EtOAc (2:1) to give the title compound (11 g, 95%).

$[\alpha]D^{25}$=−78.57 (c 0.14, $CHCl_3$);

$R_f$=0.63 (19:1, $CHCl_3$/MeOH);

Anal. Calcd. for $C_{15}H_{18}NO_4$ (M+H): 276.1235;

Found: 276.1235 (M+H, HRFABMS).

4.2 Synthesis of Pyruvyl-Proline

The protected dipeptide from the previous synthesis (11.0 g, 40 mmol) was dissolved in EtOAc (75 mL) and stirred under hydrogen over Pd/C for 2 h. The catalyst was then filtered off and the filtrate was evaporated to dryness. The residue was crystallized from EtoAc-hexane to give the unprotected peptide (6.9 g, 93):

$[\alpha]_D^{25}$=−103.99 (c 0.124, $CHCl_3$);

$R_f$=0.4163 (19:1:0.5, $CHCl_3$/MeOH/AcOH;

Anal. Calcd. for $C_8H_{12}NO_4$ (M+H): 186.0766;

Found: 186.0765 (M+H, HRFABMS).

4.3 Synthesis of Dehydrodidemnin B

EDC (1-ethyl-3-(3-dimethylaminopropyl)carbodiimide, 4.27 g, 22.3 mmol) was added to a solution of Pyrvu-Pro (8.2 g, 44.5 mmol) in dry $CH_2Cl_2$ (40 mL) at 10° C. with stirring. The mixture was stirred for 2 h at 10° C. and then cooled to 0° C. Didemnin A (1.4 g, 1.48 mmol) in $CH_2Cl_2$-DMF (10 mL, 4:1) was added, and the clear solution was stirred at 0° C. for 2 h and then left in the refrigerator overnight.

DMAP (4-dimethylaminopyridine, 25 mg) was added to the reaction mixture, and it was again left in the refrigerator for 48 h. The solvent was evaporated to dryness, and the residue was taken up in EtOAc and washed with 5% $NaHCO_3$ and water to neutral pH. The organic layer was dried ($Na_2SO_4$) and concentrated. The residue so obtained was chromatographed on silica gel using $CHCl_3$-MeOH (19:1) to give dehydrodidemnin B (1.4 g, 84%, 2 spots on TLC):

$[\alpha]_D^{25}$=−95.384 (c 0.06, $MeOH)_3$);

$R_f$=0.51 and 0.44 (19:1, $CHCl_3$/MeOH);

Anal. Calcd. for $C_{57}H_{88}N_7O_{15}$ (M+H): 1110.6338;

Found: 1110.6355 (M+H, HRFABMS).

The same series of reactions can be carried out with slight modifications, in particular EDC can be replaced by DDC with slightly lower yield.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A process for the synthetic preparation of dehydrodidemnin B, which comprises the following steps:

(a) reacting didemnin A with pyruvyl-proline; and (b) separating the resulting dehydrodidemnin B from the reaction mixture.

2. A method for isolation of dehydrodidemnin B by extraction from a dehydrodidemnin B-containing tunicate, said method comprising the steps of:

(a) extracting the tunicate *Alpidium albicans* with alcohol; and (b) isolating the compound dehydrodidemnin B from the alcoholic extract.

* * * * *

UNITED STATES PATENT AND TRADEMARK OFFICE
CERTIFICATE OF CORRECTION

| | |
|---|---|
| PATENT NO. | : 6,153,731 |
| APPLICATION NO. | : 09/183024 |
| DATED | : November 28, 2000 |
| INVENTOR(S) | : Kenneth L. Rinehart and Anna M. Lithgow-Bertelloni |

It is certified that error appears in the above-identified patent and that said Letters Patent is hereby corrected as shown below:

Title Page, Item [62], Related U.S. Application Data, line 3,

"07/844,567, Apr. 24, 1992, abandoned." should read --07/844,567, Apr. 24, 1992, abandoned, which is a 371 of PCT/GB90/01495, filed Oct. 1, 1990.--

Title Page, Item [30], Foreign Application Priority Data, line 1,

"Jan. 10, 1990 [WO] WIPO...........PCT/GB90/01495" should read

--Sept. 29, 1989 [GB] Great Britain ......................8922026.3--

Title Page, Item [57], Abstract:

"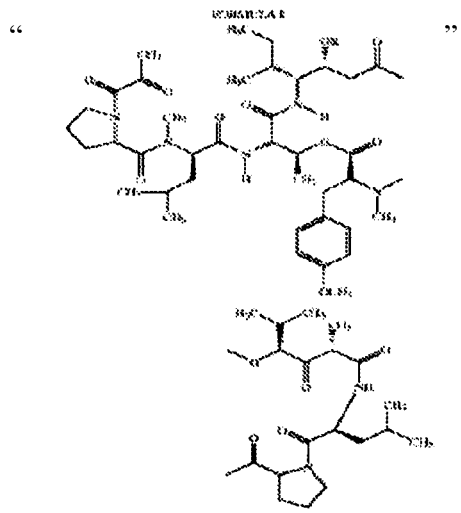"

should read

--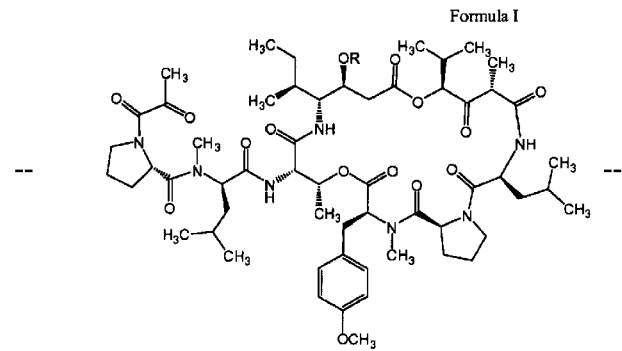--

UNITED STATES PATENT AND TRADEMARK OFFICE
CERTIFICATE OF CORRECTION

PATENT NO.       : 6,153,731
APPLICATION NO.  : 09/183024
DATED            : November 28, 2000
INVENTOR(S)      : Kenneth L. Rinehart and Anna M. Lithgow-Bertelloni It is certified that error appears in the above-identified patent and that said Letters Patent is hereby corrected as shown below:

Column 1, line 38: "terranean tunicate *Alpidium albicans*, namely dehdyrodi-"

should read --terranean tunicate *Aplidium albicans*, namely dehydrodi- --

Columns 1 and 2, lines 40-61:

"
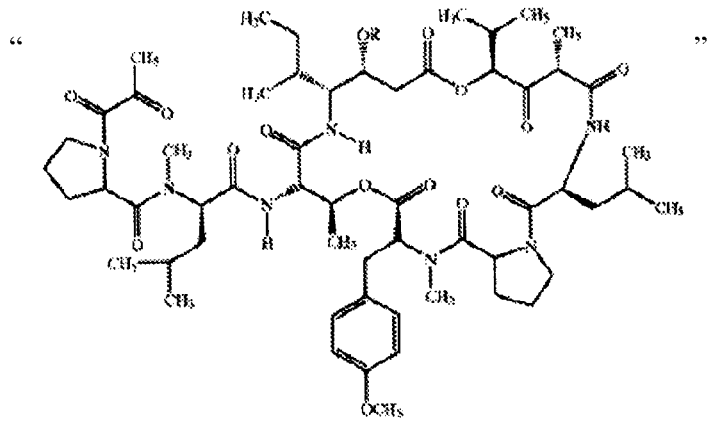
"

should read

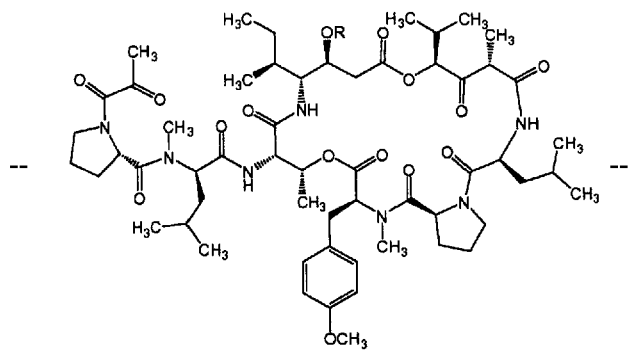

--    --

UNITED STATES PATENT AND TRADEMARK OFFICE
CERTIFICATE OF CORRECTION

PATENT NO.        : 6,153,731
APPLICATION NO. : 09/183024
DATED              : November 28, 2000
INVENTOR(S)       : Kenneth L. Rinehart and Anna M. Lithgow-Bertelloni It is certified that error appears in the above-identified patent and that said Letters Patent is hereby corrected as shown below:

Claim 2, column 12, line 39: "(a) extracting the tunicate *Alpidium albicans* with alcohol;"

should read --(a) extracting the tunicate *Aplidium albicans* with alcohol;--

Signed and Sealed this

Third Day of March, 2009

JOHN DOLL
*Acting Director of the United States Patent and Trademark Office*